US007759300B2

(12) United States Patent
Besse et al.

(10) Patent No.: US 7,759,300 B2

(45) Date of Patent: Jul. 20, 2010

(54) SOLIDIFICATION MATRIX INCLUDING A SALT OF A STRAIGHT CHAIN SATURATED MONO-, DI-, OR TRI- CARBOXYLIC ACID

(75) Inventors: Michael E. Besse, Golden Valley, MN (US); Brenda L. Tjelta, St. Paul, MN (US); Lisa M. Sanders, Eagan, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 11/772,641

(22) Filed: Jul. 2, 2007

(65) Prior Publication Data

US 2009/0011973 A1 Jan. 8, 2009

(51) Int. Cl.
*A61K 7/50* (2006.01)

(52) U.S. Cl. ....................... 510/445; 510/451; 510/511; 510/512; 510/569

(58) Field of Classification Search ................. 510/445, 510/451, 569, 511, 512
See application file for complete search history.

(56) References Cited

U.S. PATENT DOCUMENTS 4,689,167 A 8/1987 Collins et al.
4,971,714 A 11/1990 Lokkesmoe et al.
5,009,804 A 4/1991 Clayton et al.
5,719,111 A * 2/1998 van den Brom et al. ..... 510/224
5,759,976 A * 6/1998 Roach et al. ................ 510/218
6,262,010 B1 * 7/2001 Emery et al. ................ 510/446
6,638,902 B2 10/2003 Tarara et al.
6,660,707 B2 * 12/2003 Lentsch et al. ............. 510/445
6,956,019 B2 10/2005 Lentsch et al.
7,094,746 B2 8/2006 Lentsch et al.
7,186,677 B2 * 3/2007 Rahse et al. ................ 510/444
2002/0082178 A1 * 6/2002 Besse et al. ................. 510/197
2002/0177541 A1 * 11/2002 Tarara et al. ................ 510/392
2005/0113278 A1 * 5/2005 Stolte et al. ................. 510/445
2005/0233920 A1 * 10/2005 Stolte et al. ................. 510/147

OTHER PUBLICATIONS

International Search Report and Written Opinion of international application No. PCT/IB2008/052274, mailed Jan. 30,2009, 14 pp.
International Search Report issued in PCT/IB2008/055592, mailed May 26, 2009, 3 pages.

* cited by examiner

*Primary Examiner*—Milton I Cano
*Assistant Examiner*—M. Reza Asdjodi
(74) *Attorney, Agent, or Firm*—Faegre & Benson LLP

(57) ABSTRACT

A solidification matrix includes a straight chain saturated carboxylic acid salt, sodium carbonate, and water. The straight chain saturated carboxylic acid salt is selected from a salt of a mono-, di-, or tri-carboxylic acid. The solidification matrix may be used, for example, in a solid detergent composition.

19 Claims, No Drawings

SOLIDIFICATION MATRIX INCLUDING A SALT OF A STRAIGHT CHAIN SATURATED MONO-, DI-, OR TRI- CARBOXYLIC ACID

BACKGROUND

The present invention relates generally to the field of solidification and solidification matrices. In particular, the present invention relates to salts of straight chain saturated mono-, di-, and tri-carboxylic acids as part of a solidification matrix.

The use of solidification technology and solid block detergents in institutional and industrial operations was pioneered in the SOLID POWER® brand technology claimed in Fernholz et al., U.S. Reissue Pat. Nos. 32,762 and 32,818. Additionally, sodium carbonate hydrate cast solid products using substantially hydrated sodium carbonate materials was disclosed in Heile et al., U.S. Pat. Nos. 4,595,520 and 4,680,134.

In more recent years, attention has been directed to producing highly effective detergent materials from less caustic materials such as soda ash, also known as sodium carbonate. Early work in developing the sodium carbonate based detergents found that sodium carbonate hydrate-based materials often swelled, (i.e., were dimensionally unstable) after solidification. Such swelling can interfere with packaging, dispensing, and use. The dimensional instability of the solid materials relates to the unstable nature of various hydrate forms prepared in manufacturing the sodium carbonate solid materials. Early products made with hydrated sodium carbonate typically comprised of anhydrous, a one mole hydrate, a seven mole hydrate, a ten mole hydrate or more mixtures thereof. However, after the product had been manufactured and stored at ambient temperatures, the hydration state of the initial product was found to shift between hydrate forms, e.g., one, seven, and ten mole hydrates, resulting in dimensional instability of the block chemicals. In these conventional solid form compositions, changes in water content and temperature lead to structural and dimensional change, which may lead to a failure of the solid form, resulting in problems such as the inability of the solid form to fit into dispensers for use.

Additionally, conventional solid alkaline detergents, particularly those intended for institutional and commercial use, generally require phosphates in their compositions. The phosphates typically serve multiple purposes in the compositions, for example, to control the rate of solidification, to remove and suspend soils, and as an effective hardness sequestrant. It was found, disclosed, and claimed in U.S. Pat. Nos. 6,258,765, 6,156,715, 6,150,324, and 6,177,392, that a solid block functional material could be made using a binding agent that includes a carbonate salt, an organic acetate, such as an aminocarboxylate, or phosphonate component and water. Due to ecological concerns, further work has recently been directed to replacing phosphorous-containing compounds in detergents. In addition, nitrilotriacetic acid (NTA)-containing aminocarboxylate components used in place of phosphorous-containing compounds in some instances as a binding agents and hardness sequestrants, are believed to be carcinogenic. As such, their use has also been curtailed.

There is an ongoing need to provide alternative solidification technologies which are phosphorous-free and/or NTA-free. However, the lack of predictability in the solidification process and the lack of predictability of dimensional stability in solid form compositions have hampered efforts to successfully replace phosphorous and/or NTA-containing components with environmentally-friendly substitutes.

SUMMARY

A solidification matrix includes a straight chain saturated carboxylic acid salt, sodium carbonate, and water. The straight chain saturated carboxylic acid salt is selected from a salt of a mono-, di-, or tri-carboxylic acid. The solidification matrix may be used, for example, in a solid detergent composition.

DETAILED DESCRIPTION

The solidification matrix of the present invention may be employed in any of a wide variety of situations in which a dimensionally stable solid product is desired. The solidification matrix is dimensionally stable and has an appropriate rate of solidification. In addition, the solidification matrix may be substantially free of phosphorous and NTA, making the solidification matrix particularly useful in cleaning applications where it is desired to use an environmentally friendly detergent. Such applications include, but are not limited to: machine and manual warewashing, presoaks, laundry and textile cleaning and destaining, carpet cleaning and destaining, vehicle cleaning and care applications, surface cleaning and destaining, kitchen and bath cleaning and destaining, floor cleaning and destaining, cleaning in place operations, general purpose cleaning and destaining, industrial or household cleaners, and pest control agents. Methods suitable for preparing a solid detergent composition using the solidification matrix are also provided.

The solidification matrix generally includes a straight chain saturated mono-, di-, or tri-carboxylic acid salt, sodium carbonate (soda ash), and water for forming solid compositions. Suitable component concentrations for the solidification matrix range from between approximately 1% and approximately 15% by weight of a saturated straight chain saturated mono-, di-, or tri-carboxylic acid salt, between approximately 2% and approximately 50% by weight water, and between approximately 20% and approximately 70% by weight sodium carbonate. Particularly suitable component concentrations for the solidification matrix range from between approximately 1% and approximately 12% of a salt of a saturated straight chain saturated mono-, di-, or tri-carboxylic acid, between approximately 5% and approximately 40% by weight water, and between approximately 45% and approximately 65% by weight sodium carbonate. More particularly suitable component concentrations for the solidification matrix range from between approximately 1% and approximately 10% of a salt of a saturated straight chain saturated mono-, di-, or tri-carboxylic acid, between approximately 5% and approximately 35% by weight water, and between approximately 50% and approximately 60% by weight sodium carbonate. Those skilled in the art will appreciate other suitable component concentration ranges for obtaining comparable properties of the solidification matrix.

The actual solidification mechanism of the solidification matrix occurs through ash hydration, or the interaction of the sodium carbonate with water. It is believed that the straight chain saturated mono-, di-, or tri-carboxylic acid salt functions to control the kinetics and thermodynamics of the solidification process and provides a solidification matrix in which additional functional materials may be bound to form a functional solid composition. The straight chain saturated mono-, di-, or tri-carboxylic acid salt may stabilize the carbonate hydrates and the functional solid composition by acting as a donor and/or acceptor of free water. By controlling the rate of water migration for hydration of the ash, the straight chain saturated mono-, di-, or tri-carboxylic acid salt may control the rate of solidification to provide process and dimensional stability to the resulting product. The rate of solidification is significant because if the solidification matrix solidifies too quickly, the composition may solidify during mixing and stop processing. If the solidification matrix solidifies too slowly, valuable process time is lost. The straight chain saturated mono-, di-, or tri-carboxylic acid salt also provides dimensional stability to the end product by ensuring that the solid product does not swell. If the solid product swells after solidification, various problems may occur, including but not limited to: decreased density, integrity, and appearance; and inability to dispense or package the solid product. Generally, a solid product is considered to have dimensional stability if the solid product has a growth exponent of less than about 3% and particularly less than about 2%.

The straight chain saturated mono-, di-, or tri-carboxylic acid salt is combined with water prior to incorporation into the detergent composition and can be provided as a solid hydrate or as a solid salt that is solvated in an aqueous solution, e.g., in a liquid premix. However, the straight chain saturated mono-, di-, or tri-carboxylic acid salt should be in a water matrix when added to the detergent composition for the detergent composition to effectively solidify. In general, an effective amount of straight chain saturated mono-, di-, or tri-carboxylic acid salt is considered an amount that effectively controls the kinetics and thermodynamics of the solidification system by controlling the rate and movement of water. Examples of particularly suitable salts of straight chain saturated monocarboxylic acids include, but are not limited to salts of acetic acid and salts of gluconic acid. Examples of particularly suitable salts of straight chain saturated dicarboxylic acids include, but are not limited to: salts of tartartic acid, salts of malic acid, salts of succinic acid, salts of glutaric acid, and salts of adipic acid. An example of a particularly suitable salt of a straight chain saturated tricarboxylic acid includes, but is not limited to, a salt of citric acid.

Water may be independently added to the solidification matrix or may be provided in the solidification matrix as a result of its presence in an aqueous material that is added to the detergent composition. For example, materials added to the detergent composition may include water or may be prepared in an aqueous premix available for reaction with the solidification matrix component(s). Typically, water is introduced into the solidification matrix to provide the solidification matrix with a desired viscosity for processing prior to solidification and to provide a desired rate of solidification. The water may also be present as a processing aid and may be removed or become water of hydration. The water may thus be present in the form of aqueous solutions of the solidification matrix, or aqueous solutions of any of the other ingredients, and/or added aqueous medium as an aid in processing. In addition, it is expected that the aqueous medium may help in the solidification process when is desired to form the concentrate as a solid. The water may also be provided as deionized water or as softened water.

The amount of water in the resulting solid detergent composition will depend on whether the solid detergent composition is processed through forming techniques or casting (solidification occurring within a container) techniques. In general, when the components are processed by forming techniques, it is believed that the solid detergent composition can include a relatively smaller amount of water for solidification compared with the casting techniques. When preparing the solid detergent composition by forming techniques, water may be present in ranges of between about 5% and about 25% by weight, particularly between about 7% and about 20% by weight, and more particularly between about 8% and about 15% by weight. When preparing the solid detergent composition by casting techniques, water may be present in the ranges of between about 15% and about 50% by weight, particularly between about 20% and about 45% by weight, and more particularly between about 22% and about 40% by weight.

The solidification matrix and resulting solid detergent composition may also exclude phosphorus or nitrilotriacetic acid (NTA) containing compounds, to make the solid detergent composition more environmentally acceptable. Phosphorus-free refers to a composition, mixture, or ingredients to which phosphorus-containing compounds are not added. Should phosphorus-containing compounds be present through contamination of a phosphorus-free composition, mixture, or ingredient, the level of phosphorus-containing compounds in the resulting composition is less than approximately 0.5 wt %, less than approximately 0.1 wt %, and often less than approximately 0.01 wt %. NTA-free refers to a composition, mixture, or ingredients to which NTA-containing compounds are not added. Should NTA-containing compounds be present through contamination of an NTA-free composition, mixture, or ingredient, the level of NTA in the resulting composition shall be less than approximately 0.5 wt %, less than approximately 0.1 wt %, and often less than approximately 0.01 wt %. When the solidification matrix is NTA-free, the solidification matrix and resulting solid detergent composition is also compatible with chlorine, which functions as an anti-redeposition and stain-removal agent.

Additional Functional Materials

The hydrated solidification matrix, or binding agent, can be used to form a solid detergent composition including additional components or agents, such as additional functional materials. As such, in some embodiments, the solidification matrix including the straight chain saturated mono-, di-, or tri-carboxylic acid salt, water, and sodium carbonate may provide a large amount, or even all of the total weight of the detergent composition, for example, in embodiments having few or no additional functional materials disposed therein. The functional materials provide desired properties and functionalities to the solid detergent composition. For the purpose of this application, the term "functional materials" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional materials may be used. For example, many of the functional materials discussed below relate to materials used in cleaning and/or destaining applications. However, other embodiments may include functional materials for use in other applications.

Alkaline Source

The solid detergent composition can include an effective amount of one or more alkaline sources to enhance cleaning of a substrate and improve soil removal performance of the solid detergent composition. In general, it is expected that the composition will include the alkaline source in an amount of at least about 5% by weight, at least about 10% by weight, or at least about 15% by weight. In order to provide sufficient room for other components in the concentrate, the alkaline source can be provided in the concentrate in an amount of less than about 75% by weight, less than about 60% by weight, less than about 40% by weight, less than about 30% by weight, or less than about 20% by weight. The alkalinity source may constitute between about 0.1% and about 90% by weight, between about 0.5% and about 80% by weight, and between about 1% and about 60% by weight of the total weight of the solid detergent composition.

An effective amount of one or more alkaline sources should be considered as an amount that provides a use composition having a pH of at least about 8. When the use composition has a pH of between about 8 and about 10, it can be considered mildly alkaline, and when the pH is greater than about 12, the use composition can be considered caustic. In general, it is desirable to provide the use composition as a mildly alkaline cleaning composition because it is considered to be safer than the caustic based use compositions. In some circumstances, the solid detergent composition may provide a use composition that is useful at pH levels below about 8. In such compositions, the alkaline source may be omitted, and additional pH adjusting agents may be used to provide the use composition with the desired pH.

Examples of suitable alkaline sources of the solid detergent composition include, but are not limited to an alkali metal carbonate and an alkali metal hydroxide. Exemplary alkali metal carbonates that can be used include, but are not limited to: sodium or potassium carbonate, bicarbonate, sesquicarbonate, and mixtures thereof. Exemplary alkali metal hydroxides that can be used include, but are not limited to sodium, lithium, or potassium hydroxide. The alkali metal hydroxide may be added to the composition in any form known in the art, including as solid beads, dissolved in an aqueous solution, or a combination thereof. Alkali metal hydroxides are commercially available as a solid in the form of prilled solids or beads having a mix of particle sizes ranging from about 12-100 U.S. mesh, or as an aqueous solution, as for example, as a 50% and a 73% by weight solution. It is preferred that the alkali metal hydroxide is added in the form of an aqueous solution, particularly a 50% by weight hydroxide solution, to reduce the amount of heat generated in the composition due to hydration of the solid alkali material.

In addition to the first alkalinity source, the solid detergent composition may comprise a secondary alkalinity source. Examples of useful secondary alkaline sources include, but are not limited to: metal silicates such as sodium or potassium silicate or metasilicate; metal carbonates such as sodium or potassium carbonate, bicarbonate, sesquicarbonate; metal borates such as sodium or potassium borate; and ethanolamines and amines. Such alkalinity agents are commonly available in either aqueous or powdered form, either of which is useful in formulating the present solid detergent compositions.

Surfactants

The solid detergent composition can include at least one cleaning agent comprising a surfactant or surfactant system. A variety of surfactants can be used in a solid detergent composition, including, but not limited to: anionic, nonionic, cationic, and zwitterionic surfactants. Surfactants are an optional component of the solid detergent composition and can be excluded from the concentrate. Exemplary surfactants that can be used are commercially available from a number of sources. For a discussion of surfactants, see Kirk-Othmer, Encyclopedia of Chemical Technology, Third Edition, volume 8, pages 900-912. When the solid detergent composition includes a cleaning agent, the cleaning agent is provided in an amount effective to provide a desired level of cleaning. The solid detergent composition, when provided as a concentrate, can include the cleaning agent in a range of about 0.05% to about 20% by weight, about 0.5% to about 15% by weight, about 1% to about 15% by weight, about 1.5% to about 10% by weight, and about 2% to about 5% by weight. Additional exemplary ranges of surfactant in a concentrate include about 0.5% to about 5% by weight, and about 1% to about 3% by weight.

Examples of anionic surfactants useful in the solid detergent composition include, but are not limited to: carboxylates such as alkylcarboxylates and polyalkoxycarboxylates, alcohol ethoxylate carboxylates, nonylphenol ethoxylate carboxylates; sulfonates such as alkylsulfonates, alkylbenzenesulfonates, alkylarylsulfonates, sulfonated fatty acid esters; sulfates such as sulfated alcohols, sulfated alcohol ethoxylates, sulfated alkylphenols, alkylsulfates, sulfosuccinates, and alkylether sulfates. Exemplary anionic surfactants include, but are not limited to: sodium alkylarylsulfonate, alpha-olefinsulfonate, and fatty alcohol sulfates.

Examples of nonionic surfactants useful in the solid detergent composition include, but are not limited to, those having a polyalkylene oxide polymer as a portion of the surfactant molecule. Such nonionic surfactants include, but are not limited to: chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated amines such as alkoxylated ethylene diamine; alcohol alkoxylates such as alcohol ethoxylate propoxylates, alcohol propoxylates, alcohol propoxylate ethoxylate propoxylates, alcohol ethoxylate butoxylates; nonylphenol ethoxylate, polyoxyethylene glycol ether; carboxylic acid esters such as glycerol esters, polyoxyethylene esters, ethoxylated and glycol esters of fatty acids; carboxylic amides such as diethanolamine condensates, monoalkanolamine condensates, polyoxyethylene fatty acid amides; and polyalkylene oxide block copolymers. An example of a commercially available ethylene oxide/propylene oxide block copolymer includes, but is not limited to, PLURONIC®, available from BASF Corporation, Florham Park, N.J. An example of a commercially available silicone surfactant includes, but is not limited to, ABIL® B8852, available from Goldschmidt Chemical Corporation, Hopewell, Va.

Examples of cationic surfactants that can be used in the solid detergent composition include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride. The cationic surfactant can be used to provide sanitizing properties.

Examples of zwitterionic surfactants that can be used in the solid detergent composition include, but are not limited to: betaines, imidazolines, and propionates.

Because the solid detergent composition is intended to be used in an automatic dishwashing or warewashing machine, the surfactants selected, if any surfactant is used, can be those that provide an acceptable level of foaming when used inside a dishwashing or warewashing machine. Solid detergent compositions for use in automatic dishwashing or warewashing machines are generally considered to be low-foaming compositions. Low foaming surfactants that provide the desired level of detersive activity are advantageous in an environment such as a dishwashing machine where the presence of large amounts of foaming can be problematic. In addition to selecting low foaming surfactants, defoaming agents can also be utilized to reduce the generation of foam. Accordingly, surfactants that are considered low foaming surfactants can be used. In addition, other surfactants can be used in conjunction with a defoaming agent to control the level of foaming.

Some surfactants can also function as secondary solidifying agents. For example, anionic surfactants which have high melting points provide a solid at the temperature of application. Anionic surfactants which have been found most useful include, but are not limited to: linear alkyl benzene sulfonate surfactants, alcohol sulfates, alcohol ether sulfates, and alpha olefin sulfonates. Generally, linear alkyl benzene sulfonates are preferred for reasons of cost and efficiency. Amphoteric or zwitterionic surfactants are also useful in providing detergency, emulsification, wetting and conditioning properties. Representative amphoteric surfactants include, but are not limited to: N-coco-3-aminopropionic acid and acid salts, N-tallow-3-iminodiproprionate salts, N-lauryl-3-iminodiproprionate disodium salt, N-carboxymethyl-N-cocoalkyl-N-dimethylammonium hydroxide, N-carboxymethyl-N-dimethyl-N-(9-octadecenyl)ammonium hydroxide, (1-carboxyheptadecyl) trimethylammonium hydroxide, (1-carboxyundecyl)trimethylammonium hydroxide, N-cocoamidoethyl-N-hydroxyethylglycine sodium salt, N-hydroxyethyl-N-stearamidoglycine sodium salt, N-hydroxyethyl-N-lauramido-.beta.-alanine sodium salt, N-cocoamido-N-hydroxyethyl-.beta.-alanine sodium salt, mixed alcyclic amines and their ethoxylated and sulfated sodium salts, 2-alkyl-1-carboxymethyl-1-hydroxyethyl-2-imidazolinium hydroxide sodium salt or free acid wherein the alkyl group may be nonyl, undecyl, and heptadecyl. Other useful amphoteric surfactants include, but are not limited to: 1,1-bis(carboxymethyl)-2-undecyl-2-imidazolinium hydroxide disodium salt and oleic acid-ethylenediamine condensate, propoxylated and sulfated sodium salt, and amine oxide amphoteric surfactants.

Builders or Water Conditioners

The solid detergent composition can include one or more building agents, also called chelating or sequestering agents (e.g., builders), including, but not limited to: a condensed phosphate, a phosphonate, an aminocarboxylic acid, or a polyacrylate. In addition, when sodium citrate is included in the solid detergent composition, the sodium citrate may also function as a builder. In general, a chelating agent is a molecule capable of coordinating (i.e., binding) the metal ions commonly found in natural water to prevent the metal ions from interfering with the action of the other detersive ingredients of a cleaning composition. Preferable levels of addition for builders that can also be chelating or sequestering agents are between about 0.1% to about 70% by weight, about 1% to about 60% by weight, or about 1.5% to about 50% by weight. If the solid detergent is provided as a concentrate, the concentrate can include between approximately 1% to approximately 60% by weight, between approximately 3% to approximately 50% by weight, and between approximately 6% to approximately 45% by weight of the builders. Additional ranges of the builders include between approximately 3% to approximately 20% by weight, between approximately 6% to approximately 15% by weight, between approximately 25% to approximately 50% by weight, and between approximately 35% to approximately 45% by weight.

Examples of condensed phosphates include, but are not limited to: sodium and potassium orthophosphate, sodium and potassium pyrophosphate, sodium tripolyphosphate, and sodium hexametaphosphate. A condensed phosphate may also assist, to a limited extent, in solidification of the solid detergent composition by fixing the free water present in the composition as water of hydration.

Examples of phosphonates included, but are not limited to: 1-hydroxyethane-1,1-diphosphonic acid, $CH_2C(OH)[PO(OH)_2]_2$; aminotri(methylenephosphonic acid), $N[CH_2PO(OH)_2]_3$; aminotri(methylenephosphonate), sodium salt (ATMP), $N[CH_2PO(ONa)_2]_3$; 2-hydroxyethyliminobis(methylenephosphonic acid), $HOCH_2CH_2N[CH_2PO(OH)_2]_2$; diethylenetriaminepenta(methylenephosphonic acid), $(HO)_2POCH_2N[CH_2CH_2N[CH_2PO(OH)_2]_2]_2$; diethylenetriaminepenta(methylenephosphonate), sodium salt (DTPMP), $C_9H_{(28-x)}N_3Na_xO_{15}P_5$ (x=7); hexamethylenediamine(tetramethylenephosphonate), potassium salt, $C_{10}H_{(28-x)}N_2K_xO_{12}P_4$ (x=6); bis(hexamethylene)triamine(pentamethylenephosphonic acid), $(HO_2)POCH_2N[(CH_2)_2N[CH_2PO(OH)_2]_2]_2$; and phosphorus acid, $H_3PO_3$. A preferred phosphonate combination is ATMP and DTPMP. A neutralized or alkaline phosphonate, or a combination of the phosphonate with an alkali source prior to being added into the mixture such that there is little or no heat or gas generated by a neutralization reaction when the phosphonate is added is preferred.

The solid detergent compositions can contain a non-phosphorus based builder. Although various components may include trace amounts of phosphorous, a composition that is considered free of phosphorous generally does not include phosphate or phosphonate builder or chelating components as an intentionally added component. Carboxylates such as citrate or gluconate are suitable. Useful aminocarboxylic acid materials containing little or no NTA include, but are not limited to: N-hydroxyethylaminodiacetic acid, ethylenediaminetetraacetic acid (EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), and other similar acids having an amino group with a carboxylic acid substituent.

Water conditioning polymers can be used as non-phosphorus containing builders. Exemplary water conditioning polymers include, but are not limited to: polycarboxylates. Exemplary polycarboxylates that can be used as builders and/or water conditioning polymers include, but are not limited to: those having pendant carboxylate ($-CO_2^-$) groups such as polyacrylic acid, maleic acid, maleic/olefin copolymer, sulfonated copolymer or terpolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, and hydrolyzed acrylonitrile-methacrylonitrile copolymers. For a further discussion of chelating agents/sequestrants, see Kirk-Othmer, Encyclopedia of Chemical Technology, Third Edition, volume 5, pages 339-366 and volume 23, pages 319-320, the disclosure of which is incorporated by reference herein. These materials may also be used at substoichiometric levels to function as crystal modifiers

Hardening Agents

The solid detergent compositions can also include a hardening agent in addition to, or in the form of, the builder. A hardening agent is a compound or system of compounds, organic or inorganic, which significantly contributes to the uniform solidification of the composition. Preferably, the hardening agents are compatible with the cleaning agent and other active ingredients of the composition and are capable of providing an effective amount of hardness and/or aqueous solubility to the processed composition. The hardening agents should also be capable of forming a homogeneous matrix with the cleaning agent and other ingredients when mixed and solidified to provide a uniform dissolution of the cleaning agent from the solid detergent composition during use.

The amount of hardening agent included in the solid detergent composition will vary according to factors including, but not limited to: the type of solid detergent composition being prepared, the ingredients of the solid detergent composition, the intended use of the composition, the quantity of dispensing solution applied to the solid composition over time during use, the temperature of the dispensing solution, the hardness of the dispensing solution, the physical size of the solid detergent composition, the concentration of the other ingredients, and the concentration of the cleaning agent in the composition. It is preferred that the amount of the hardening agent included in the solid detergent composition is effective to combine with the cleaning agent and other ingredients of the composition to form a homogeneous mixture under continuous mixing conditions and a temperature at or below the melting temperature of the hardening agent.

It is also preferred that the hardening agent form a matrix with the cleaning agent and other ingredients which will harden to a solid form under ambient temperatures of approximately 30° C. to approximately 50° C., particularly approximately 35° C. to approximately 45° C., after mixing ceases and the mixture is dispensed from the mixing system, within approximately 1 minute to approximately 3 hours, particularly approximately 2 minutes to approximately 2 hours, and particularly approximately 5 minutes to approximately 1 hour. A minimal amount of heat from an external source may be applied to the mixture to facilitate processing of the mixture. It is preferred that the amount of the hardening agent included in the solid detergent composition is effective to provide a desired hardness and desired rate of controlled solubility of the processed composition when placed in an aqueous medium to achieve a desired rate of dispensing the cleaning agent from the solidified composition during use.

The hardening agent may be an organic or an inorganic hardening agent. A preferred organic hardening agent is a polyethylene glycol (PEG) compound. The solidification rate of solid detergent compositions comprising a polyethylene glycol hardening agent will vary, at least in part, according to the amount and the molecular weight of the polyethylene glycol added to the composition. Examples of suitable polyethylene glycols include, but are not limited to: solid polyethylene glycols of the general formula $H(OCH_2CH_2)_nOH$, where n is greater than 15, particularly approximately 30 to approximately 1700. Typically, the polyethylene glycol is a solid in the form of a free-flowing powder or flakes, having a molecular weight of approximately 1,000 to approximately 100,000, particularly having a molecular weight of at least approximately 1,450 to approximately 20,000, more particularly between approximately 1,450 to approximately 8,000. The polyethylene glycol is present at a concentration of from approximately 1% to 75% by weight and particularly approximately 3% to approximately 15% by weight. Suitable polyethylene glycol compounds include, but are not limited to: PEG 4000, PEG 1450, and PEG 8000 among others, with PEG 4000 and PEG 8000 being most preferred. An example of a commercially available solid polyethylene glycol includes, but is not limited to: CARBOWAX, available from Union Carbide Corporation, Houston, Tex.

Preferred inorganic hardening agents are hydratable inorganic salts, including, but not limited to: sulfates and bicarbonates. The inorganic hardening agents are present at concentrations of up to approximately 50% by weight, particularly approximately 5% to approximately 25% by weight, and more particularly approximately 5% to approximately 15% by weight.

Urea particles can also be employed as hardeners in the solid detergent compositions. The solidification rate of the compositions will vary, at least in part, to factors including, but not limited to: the amount, the particle size, and the shape of the urea added to the composition. For example, a particulate form of urea can be combined with a cleaning agent and other ingredients, and preferably a minor but effective amount of water. The amount and particle size of the urea is effective to combine with the cleaning agent and other ingredients to form a homogeneous mixture without the application of heat from an external source to melt the urea and other ingredients to a molten stage. It is preferred that the amount of urea included in the solid detergent composition is effective to provide a desired hardness and desired rate of solubility of the composition when placed in an aqueous medium to achieve a desired rate of dispensing the cleaning agent from the solidified composition during use. In some embodiments, the composition includes between approximately 5% to approximately 90% by weight urea, particularly between approximately 8% and approximately 40% by weight urea, and more particularly between approximately 10% and approximately 30% by weight urea.

The urea may be in the form of prilled beads or powder. Prilled urea is generally available from commercial sources as a mixture of particle sizes ranging from about 8-15 U.S. mesh, as for example, from Arcadian Sohio Company, Nitrogen Chemicals Division. A prilled form of urea is preferably milled to reduce the particle size to about 50 U.S. mesh to about 125 U.S. mesh, particularly about 75-100 U.S. mesh, preferably using a wet mill such as a single or twin-screw extruder, a Teledyne mixer, a Ross emulsifier, and the like.

Bleaching Agents

Bleaching agents suitable for use in the solid detergent composition for lightening or whitening a substrate include bleaching compounds capable of liberating an active halogen species, such as $Cl_2$, $Br_2$, $-OCl^-$ and/or $-OBr^-$, under conditions typically encountered during the cleansing process. Suitable bleaching agents for use in the solid detergent compositions include, but are not limited to: chlorine-containing compounds such as chlorines, hypochlorites, or chloramines. Exemplary halogen-releasing compounds include, but are not limited to: the alkali metal dichloroisocyanurates, chlorinated trisodium phosphate, the alkali metal hypochlorites, monochloramine, and dichloramine. Encapsulated chlorine sources may also be used to enhance the stability of the chlorine source in the composition (see, for example, U.S. Pat. Nos. 4,618,914 and 4,830,773, the disclosure of which is incorporated by reference herein). A bleaching agent may also be a peroxygen or active oxygen source such as hydrogen peroxide, perborates, sodium carbonate peroxyhydrate, potassium permonosulfate, and sodium perborate mono and tetrahydrate, with and without activators such as tetraacetylethylene diamine. When the concentrate includes a bleaching agent, it can be included in an amount of between approximately 0.1% and approximately 60% by weight, between approximately 1% and approximately 20% by weight, between approximately 3% and approximately 8% by weight, and between approximately 3% and approximately 6% by weight.

Fillers

The solid detergent composition can include an effective amount of detergent fillers which do not perform as a cleaning agent per se, but cooperates with the cleaning agent to enhance the overall cleaning capacity of the composition. Examples of detergent fillers suitable for use in the present cleaning compositions include, but are not limited to: sodium sulfate, sodium chloride, starch, and sugars. When the concentrate includes a detergent filler, it can be included in an amount up to approximately 50% by weight, between approximately 1% and approximately 30% by weight, or between approximately 1.5% and approximately 25% by weight.

Defoaming Agents

A defoaming agent for reducing the stability of foam may also be included in the warewashing composition. Examples of defoaming agents include, but are not limited to: ethylene oxide/propylene block copolymers such as those available under the name Pluronic N-3; silicone compounds such as silica dispersed in polydimethylsiloxane, polydimethylsiloxane, and functionalized polydimethylsiloxane such as those available under the name Abil B9952; fatty amides, hydrocarbon waxes, fatty acids, fatty esters, fatty alcohols, fatty acid soaps, ethoxylates, mineral oils, polyethylene glycol esters, and alkyl phosphate esters such as monostearyl phosphate. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated herein by reference. When the concentrate includes a defoaming agent, the defoaming agent can be provided in an amount of between approximately 0.0001% and approximately 10% by weight, between approximately 0.001% and approximately 5% by weight, or between approximately 0.01% and approximately 1.0% by weight.

Anti-Redeposition Agents

The solid detergent composition can include an anti-redeposition agent for facilitating sustained suspension of soils in a cleaning solution and preventing the removed soils from being redeposited onto the substrate being cleaned. Examples of suitable anti-redeposition agents include, but are not limited to: polyacrylates, styrene maleic anhydride copolymers, cellulosic derivatives such as hydroxyethyl cellulose, and hydroxypropyl cellulose. When the concentrate includes an anti-redeposition agent, the anti-redeposition agent can be included in an amount of between approximately 0.5% and approximately 10% by weight, and between approximately 1% and approximately 5% by weight.

Stabilizing Agents

The solid detergent composition may also include stabilizing agents. Examples of suitable stabilizing agents include, but are not limited to: borate, calcium/magnesium ions, propylene glycol, and mixtures thereof. The concentrate need not include a stabilizing agent, but when the concentrate includes a stabilizing agent, it can be included in an amount that provides the desired level of stability of the concentrate. Exemplary ranges of the stabilizing agent include up to approximately 20% by weight, between approximately 0.5% and approximately 15% by weight, and between approximately 2% and approximately 10% by weight.

Dispersants

The solid detergent composition may also include dispersants. Examples of suitable dispersants that can be used in the solid detergent composition include, but are not limited to: maleic acid/olefin copolymers, polyacrylic acid, and mixtures thereof. The concentrate need not include a dispersant, but when a dispersant is included it can be included in an amount that provides the desired dispersant properties. Exemplary ranges of the dispersant in the concentrate can be up to approximately 20% by weight, between approximately 0.5% and approximately 15% by weight, and between approximately 2% and approximately 9% by weight.

Enzymes

Enzymes that can be included in the solid detergent composition include those enzymes that aid in the removal of starch and/or protein stains. Exemplary types of enzymes include, but are not limited to: proteases, alpha-amylases, and mixtures thereof. Exemplary proteases that can be used include, but are not limited to: those derived from *Bacillus licheniformix, Bacillus lenus, Bacillus alcalophilus*, and *Bacillus amyloliquefacins*. Exemplary alpha-amylases include *Bacillus subtilis, Bacillus amyloliquefaceins* and *Bacillus licheniformis*. The concentrate need not include an enzyme, but when the concentrate includes an enzyme, it can be included in an amount that provides the desired enzymatic activity when the solid detergent composition is provided as a use composition. Exemplary ranges of the enzyme in the concentrate include up to approximately 15% by weight, between approximately 0.5% to approximately 10% by weight, and between approximately 1% to approximately 5% by weight.

Glass and Metal Corrosion Inhibitors

The solid detergent composition can include a metal corrosion inhibitor in an amount up to approximately 50% by weight, between approximately 1% and approximately 40% by weight, or between approximately 3% and approximately 30% by weight. The corrosion inhibitor is included in the solid detergent composition in an amount sufficient to provide a use solution that exhibits a rate of corrosion and/or etching of glass that is less than the rate of corrosion and/or etching of glass for an otherwise identical use solution except for the absence of the corrosion inhibitor. It is expected that the use solution will include at least approximately 6 parts per million (ppm) of the corrosion inhibitor to provide desired corrosion inhibition properties. It is expected that larger amounts of corrosion inhibitor can be used in the use solution without deleterious effects. It is expected that at a certain point, the additive effect of increased corrosion and/or etching resistance with increasing corrosion inhibitor concentration will be lost, and additional corrosion inhibitor will simply increase the cost of using the solid detergent composition. The use solution can include between approximately 6 ppm and approximately 300 ppm of the corrosion inhibitor, and between approximately 20 ppm and approximately 200 ppm of the corrosion inhibitor. Examples of suitable corrosion inhibitors include, but are not limited to: a combination of a source of aluminum ion and a source of zinc ion, as well as an alkaline metal silicate or hydrate thereof.

The corrosion inhibitor can refer to the combination of a source of aluminum ion and a source of zinc ion. The source of aluminum ion and the source of zinc ion provide aluminum ion and zinc ion, respectively, when the solid detergent composition is provided in the form of a use solution. The amount of the corrosion inhibitor is calculated based upon the combined amount of the source of aluminum ion and the source of zinc ion. Anything that provides an aluminum ion in a use solution can be referred to as a source of aluminum ion, and anything that provides a zinc ion when provided in a use solution can be referred to as a source of zinc ion. It is not necessary for the source of aluminum ion and/or the source of zinc ion to react to form the aluminum ion and/or the zinc ion.

Aluminum ions can be considered a source of aluminum ion, and zinc ions can be considered a source of zinc ion. The source of aluminum ion and the source of zinc ion can be provided as organic salts, inorganic salts, and mixtures thereof. Exemplary sources of aluminum ion include, but are not limited to: aluminum salts such as sodium aluminate, aluminum bromide, aluminum chlorate, aluminum chloride, aluminum iodide, aluminum nitrate, aluminum sulfate, aluminum acetate, aluminum formate, aluminum tartrate, aluminum lactate, aluminum oleate, aluminum bromate, aluminum borate, aluminum potassium sulfate, aluminum zinc sulfate, and aluminum phosphate. Exemplary sources of zinc ion include, but are not limited to: zinc salts such as zinc chloride, zinc sulfate, zinc nitrate, zinc iodide, zinc thiocyanate, zinc fluorosilicate, zinc dichromate, zinc chlorate, sodium zincate, zinc gluconate, zinc acetate, zinc benzoate, zinc citrate, zinc lactate, zinc formate, zinc bromate, zinc bromide, zinc fluoride, zinc fluorosilicate, and zinc salicylate.

The applicants discovered that by controlling the ratio of the aluminum ion to the zinc ion in the use solution, it is possible to provide reduced corrosion and/or etching of glassware and ceramics compared with the use of either component alone. That is, the combination of the aluminum ion and the zinc ion can provide a synergy in the reduction of corrosion and/or etching. The ratio of the source of aluminum ion to the source of zinc ion can be controlled to provide a synergistic effect. In general, the weight ratio of aluminum ion to zinc ion in the use solution can be between at least approximately 6:1, can be less than approximately 1:20, and can be between approximately 2:1 and approximately 1:15.

An effective amount of an alkaline metal silicate or hydrate thereof can be employed in the compositions and processes of the invention to form a stable solid detergent composition having metal protecting capacity. The silicates employed in the compositions of the invention are those that have conventionally been used in solid detergent formulations. For example, typical alkali metal silicates are those powdered, particulate or granular silicates which are either anhydrous or preferably which contain water of hydration (approximately 5% to approximately 25% by weight, particularly approximately 15% to approximately 20% by weight water of hydration). These silicates are preferably sodium silicates and have a $Na_2O:SiO_2$ ratio of approximately 1:1 to approximately 1:5, respectively, and typically contain available water in the amount of from approximately 5% to approximately 25% by weight. In general, the silicates have a $Na_2O:SiO_2$ ratio of approximately 1:1 to approximately 1:3.75, particularly approximately 1:1.5 to approximately 1:3.75 and most particularly approximately 1:1.5 to approximately 1:2.5. A silicate with a $Na_2O:SiO_2$ ratio of approximately 1:2 and approximately 16% to approximately 22% by weight water of hydration, is most preferred. For example, such silicates are available in powder form as GD Silicate and in granular form as Britesil H-20, available from PQ Corporation, Valley Forge, Pa. These ratios may be obtained with single silicate compositions or combinations of silicates which upon combination result in the preferred ratio. The hydrated silicates at preferred ratios, a $Na_2O:SiO_2$ ratio of approximately 1:1.5 to approximately 1:2.5, have been found to provide the optimum metal protection and rapidly form a solid detergent. Hydrated silicates are preferred.

Silicates can be included in the solid detergent composition to provide for metal protection but are additionally known to provide alkalinity and additionally function as anti-redeposition agents. Exemplary silicates include, but are not limited to: sodium silicate and potassium silicate. The solid detergent composition can be provided without silicates, but when silicates are included, they can be included in amounts that provide for desired metal protection. The concentrate can include silicates in amounts of at least approximately 1% by weight, at least approximately 5% by weight, at least approximately 10% by weight, and at least approximately 15% by weight. In addition, in order to provide sufficient room for other components in the concentrate, the silicate component can be provided at a level of less than approximately 35% by weight, less than approximately 25% by weight, less than approximately 20% by weight, and less than approximately 15% by weight.

Fragrances and Dyes

Various dyes, odorants including perfumes, and other aesthetic enhancing agents can also be included in the composition. Suitable dyes that may be included to alter the appearance of the composition, include, but are not limited to: Direct Blue 86, available from Mac Dye-Chem Industries, Ahmedabad, India; Fastusol Blue, available from Mobay Chemical Corporation, Pittsburgh, Pa.; Acid Orange 7, available from American Cyanamid Company, Wayne, N.J.; Basic Violet 10 and Sandolan Blue/Acid Blue 182, available from Sandoz, Princeton, N.J.; Acid Yellow 23, available from Chemos GmbH, Regenstauf, Germany; Acid Yellow 17, available from Sigma Chemical, St. Louis, Mo.; Sap Green and Metanil Yellow, available from Keyston Analine and Chemical, Chicago, Ill.; Acid Blue 9, available from Emerald Hilton Davis, LLC, Cincinnati, Ohio; Hisol Fast Red and Fluorescein, available from Capitol Color and Chemical Company, Newark, N.J.; and Acid Green 25, Ciba Specialty Chemicals Corporation, Greenboro, N.C.

Fragrances or perfumes that may be included in the compositions include, but are not limited to: terpenoids such as citronellol, aldehydes such as amyl cinnamaldehyde, a jasmine such as C1S-jasmine or jasmal, and vanillin.

Thickeners

The solid detergent compositions can include a rheology modifier or a thickener. The rheology modifier may provide the following functions: increasing the viscosity of the compositions; increasing the particle size of liquid use solutions when dispensed through a spray nozzle; providing the use solutions with vertical cling to surfaces; providing particle suspension within the use solutions; or reducing the evaporation rate of the use solutions.

The rheology modifier may provide a use composition that is pseudo plastic, in other words the use composition or material when left undisturbed (in a shear mode), retains a high viscosity. However, when sheared, the viscosity of the material is substantially but reversibly reduced. After the shear action is removed, the viscosity returns. These properties permit the application of the material through a spray head. When sprayed through a nozzle, the material undergoes shear as it is drawn up a feed tube into a spray head under the influence of pressure and is sheared by the action of a pump in a pump action sprayer. In either case, the viscosity can drop to a point such that substantial quantities of the material can be applied using the spray devices used to apply the material to a soiled surface. However, once the material comes to rest on a soiled surface, the materials can regain high viscosity to ensure that the material remains in place on the soil. Preferably, the material can be applied to a surface resulting in a substantial coating of the material that provides the cleaning components in sufficient concentration to result in lifting and removal of the hardened or baked-on soil. While in contact with the soil on vertical or inclined surfaces, the thickeners in conjunction with the other components of the cleaner minimize dripping, sagging, slumping or other movement of the material under the effects of gravity. The material should be formulated such that the viscosity of the material is adequate to maintain contact between substantial quantities of the film of the material with the soil for at least a minute, particularly five minutes or more.

Examples of suitable thickeners or rheology modifiers are polymeric thickeners including, but not limited to: polymers or natural polymers or gums derived from plant or animal sources. Such materials may be polysaccharides such as large polysaccharide molecules having substantial thickening capacity. Thickeners or rheology modifiers also include clays.

A substantially soluble polymeric thickener can be used to provide increased viscosity or increased conductivity to the use compositions. Examples of polymeric thickeners for the aqueous compositions of the invention include, but are not limited to: carboxylated vinyl polymers such as polyacrylic acids and sodium salts thereof, ethoxylated cellulose, polyacrylamide thickeners, cross-linked, xanthan compositions, sodium alginate and algin products, hydroxypropyl cellulose, hydroxyethyl cellulose, and other similar aqueous thickeners that have some substantial proportion of water solubility. Examples of suitable commercially available thickeners include, but are not limited to: Acusol, available from Rohm & Haas Company, Philadelphia, Pa.; and Carbopol, available from B.F. Goodrich, Charlotte, N.C.

Examples of suitable polymeric thickeners include, but not limited to: polysaccharides. An example of a suitable commercially available polysaccharide includes, but is not limited to, Diutan, available from Kelco Division of Merck, San Diego, Calif. Thickeners for use in the solid detergent compositions further include polyvinyl alcohol thickeners, such as, fully hydrolyzed (greater than 98.5 mol acetate replaced with the —OH function).

An example of a particularly suitable polysaccharide includes, but is not limited to, xanthans. Such xanthan polymers are preferred due to their high water solubility, and great thickening power. Xanthan is an extracellular polysaccharide of xanthomonas campestras. Xanthan may be made by fermentation based on corn sugar or other corn sweetener byproducts. Xanthan comprises a poly beta-(1-4)-D-Glucopyranosyl backbone chain, similar to that found in cellulose. Aqueous dispersions of xanthan gum and its derivatives exhibit novel and remarkable rheological properties. Low concentrations of the gum have relatively high viscosities which permit it to be used economically. Xanthan gum solutions exhibit high pseudo plasticity, i.e. over a wide range of concentrations, rapid shear thinning occurs that is generally understood to be instantaneously reversible. Non-sheared materials have viscosities that appear to be independent of the pH and independent of temperature over wide ranges. Preferred xanthan materials include crosslinked xanthan materials. Xanthan polymers can be crosslinked with a variety of known covalent reacting crosslinking agents reactive with the hydroxyl functionality of large polysaccharide molecules and can also be crosslinked using divalent, trivalent or polyvalent metal ions. Such crosslinked xanthan gels are disclosed in U.S. Pat. No. 4,782,901, which is herein incorporated by reference. Suitable crosslinking agents for xanthan materials include, but are not limited to: metal cations such as Al+3, Fe+3, Sb+3, Zr+4 and other transition metals. Examples of suitable commercially available xanthans include, but are not limited to: KELTROL®, KELZAN® AR, KELZAN® D35, KELZAN® S, KELZAN® XZ, available from Kelco Division of Merck, San Diego, Calif. Known organic crosslinking agents can also be used. A preferred crosslinked xanthan is KELZAN® AR, which provides a pseudo plastic use solution that can produce large particle size mist or aerosol when sprayed.

Methods of Use

In general, a solid detergent composition using the solidification matrix of the present invention can be created by combining a salt of a straight chain saturated mono-, di-, or tri-carboxylic acid, sodium carbonate, water, and any additional functional components and allowing the components to interact and solidify. For example, in a first embodiment, the solid detergent composition may include a salt of a straight chain saturated mono-, di-, or tri-carboxylic acid, water, builder, sodium carbonate, and surfactant. In an exemplary embodiment, the solid detergent composition includes between about 1% and about 15% straight chain saturated mono-, di-, or tri-carboxylic acid salt by weight and particularly between about 1% and about 10% straight chain saturated mono-, di-, or tri-carboxylic acid salt by weight. In another exemplary embodiment, the solid detergent composition includes between about 2% and about 50% water by weight and particularly between about 5% and about 40% water by weight. In another exemplary embodiment, the solid detergent composition includes less than about 40% builder by weight and particularly less than about 30% builder by weight. In another exemplary embodiment, the solid detergent composition includes between about 20% and about 70% sodium carbonate by weight and particularly between about 45% and about 65% sodium carbonate by weight. In another exemplary embodiment, the solid detergent composition includes between about 0.5% and about 10% surfactant by weight and particularly between about 1% and about 5% surfactant by weight.

In some embodiments, the relative amounts of water and straight chain saturated mono-, di-, or tri-carboxylic acid salt are controlled within a composition. The solidification matrix and additional functional components harden into solid form due to the chemical reaction of the sodium carbonate with the water. As the solidification matrix solidifies, a binder composition can form to bind and solidify the components. At least a portion of the ingredients associate to form the binder while the balance of the ingredients forms the remainder of the solid composition. The solidification process may last from a few minutes to about six hours, depending on factors including, but not limited to: the size of the formed or cast composition, the ingredients of the composition, and the temperature of the composition.

Solid detergent compositions formed using the solidification matrix are produced using a batch or continuous mixing system. In an exemplary embodiment, a single- or twin-screw extruder is used to combine and mix one or more cleaning agents at high shear to form a homogeneous mixture. In some embodiments, the processing temperature is at or below the melting temperature of the components. The processed mixture may be dispensed from the mixer by forming, casting or other suitable means, whereupon the detergent composition hardens to a solid form. The structure of the matrix may be characterized according to its hardness, melting point, material distribution, crystal structure, and other like properties according to known methods in the art. Generally, a solid detergent composition processed according to the method of the invention is substantially homogeneous with regard to the distribution of ingredients throughout its mass and is dimensionally stable.

Specifically, in a forming process, the liquid and solid components are introduced into the final mixing system and are continuously mixed until the components form a substantially homogeneous semi-solid mixture in which the components are distributed throughout its mass. In an exemplary embodiment, the components are mixed in the mixing system for at least approximately 5 seconds. The mixture is then discharged from the mixing system into, or through, a die or other shaping means. The product is then packaged. In an exemplary embodiment, the formed composition begins to harden to a solid form in between approximately 1 minute and approximately 3 hours. Particularly, the formed composition begins to harden to a solid form in between approximately 1 minute and approximately 2 hours. More particularly, the formed composition begins to harden to a solid form in between approximately 1 minute and approximately 20 minutes.

Specifically, in a casting process, the liquid and solid components are introduced into the final mixing system and are continuously mixed until the components form a substantially homogeneous liquid mixture in which the components are distributed throughout its mass. In an exemplary embodiment, the components are mixed in the mixing system for at least approximately 60 seconds. Once the mixing is complete, the product is transferred to a packaging container where solidification takes place. In an exemplary embodiment, the cast composition begins to harden to a solid form in between approximately 1 minute and approximately 3 hours. Particularly, the cast composition begins to harden to a solid form in between approximately 1 minute and approximately 2 hours. More particularly, the cast composition begins to harden to a solid form in between approximately 1 minute and approximately 20 minutes.

By the term “solid form”, it is meant that the hardened composition will not flow and will substantially retain its shape under moderate stress or pressure or mere gravity. The degree of hardness of the solid cast composition may range from that of a fused solid product which is relatively dense and hard, for example, like concrete, to a consistency characterized as being a hardened paste. In addition, the term “solid” refers to the state of the detergent composition under the expected conditions of storage and use of the solid detergent composition. In general, it is expected that the detergent composition will remain in solid form when exposed to temperatures of up to approximately 100° F. and particularly greater than approximately 120° F.

The resulting solid detergent composition may take forms including, but not limited to: a cast solid product; an extruded, molded or formed solid pellet, block, tablet, powder, granule, flake; or the formed solid can thereafter be ground or formed into a powder, granule, or flake. In an exemplary embodiment, extruded pellet materials formed by the solidification matrix have a weight of between approximately 50 grams and approximately 250 grams, extruded solids formed by the solidification matrix have a weight of approximately 100 grams or greater, and solid block detergents formed by the solidification matrix have a mass of between approximately 1 and approximately 10 kilograms. The solid compositions provide for a stabilized source of functional materials. In some embodiments, the solid composition may be dissolved, for example, in an aqueous or other medium, to create a concentrated and/or use solution. The solution may be directed to a storage reservoir for later use and/or dilution, or may be applied directly to a point of use.

In certain embodiments, the solid detergent composition is provided in the form of a unit dose. A unit dose refers to a solid detergent composition unit sized so that the entire unit is used during a single washing cycle. When the solid detergent composition is provided as a unit dose, it is typically provided as a cast solid, an extruded pellet, or a tablet having a size of between approximately 1 gram and approximately 50 grams.

In other embodiments, the solid detergent composition is provided in the form of a multiple-use solid, such as a block or a plurality of pellets, and can be repeatedly used to generate aqueous detergent compositions for multiple washing cycles. In certain embodiments, the solid detergent composition is provided as a cast solid, an extruded block, or a tablet having a mass of between approximately 5 grams and approximately 10 kilograms. In certain embodiments, a multiple-use form of the solid detergent composition has a mass between approximately 1 kilogram and approximately 10 kilograms. In further embodiments, a multiple-use form of the solid detergent composition has a mass of between approximately 5 kilograms and about approximately 8 kilograms. In other embodiments, a multiple-use form of the solid detergent composition has a mass of between about approximately 5 grams and approximately 1 kilogram, or between approximately 5 grams and approximately 500 grams.

Although the detergent composition is discussed as being formed into a solid product, the detergent composition may also be provided in the form of a paste. When the concentrate is provided in the form of a paste, enough water is added to the detergent composition such that complete solidification of the detergent composition is precluded. In addition, dispersants and other components may be incorporated into the detergent composition in order to maintain a desired distribution of components.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

The following test method was used to characterize the compositions produced in Examples 1, 2, and 3 and Comparative Example A:

Dimensional Stability Test for Formed Products

Approximately 50 grams batch of the product using a straight chain saturated mono-, di-, or tri-carboxylic acid salt as part of the solidification matrix was first pressed in a die at approximately 1000 pounds per square inch (psi) for approximately 20 seconds to form tablets. The diameter and height of the tablets were measured and recorded. The tablets were maintained at room temperature for one day and then placed in an oven at a temperature of approximately 120° F. After the tablets were removed from the oven, the diameters and heights of the tablets were measured and recorded. The tablets were considered to exhibit dimensional stability if there was less than approximately 2% swelling, or growth.

Examples 1, 2 and 3 and Comparative Example A

Examples 1, 2, and 3 are compositions of the present invention using a straight chain saturated mono-, di-, or tri-carboxylic acid salt as part of a solidification matrix. In particular, the compositions of Examples 1, 2, and 3 used sodium citrate dihydrate, sodium tartrate dihydrate, and sodium acetate, respectively, as part of the solidification matrix. In addition, the compositions of Examples 1-3 also included component concentrations (in weight percent) of sodium carbonate (soda ash or dense ash), sodium bicarbonate, anhydrous metasilicate, a builder, and surfactants as provided in Table 1. The sodium carbonate, sodium bicarbonate, anhydrous metasilicate, sodium citrate dihydrate, copolymer, and surfactants were premixed to form a powder premix and the straight chain saturated mono-, di-, or tri-carboxylic acid salt and water were premixed to form a liquid premix. The powder premix and the liquid premix were then mixed together to form the composition. Approximately 50 grams of the composition were pressed into a tablet at approximately 1000 psi for approximately 20 seconds.

The composition of Comparative Example A was prepared as in Examples 1, 2, and 3, except that the composition of Comparative Example A did not include a straight chain saturated mono-, di-, or tri-carboxylic acid salt.

Table 1 provides the component concentrations for the compositions of Example 1, Example 2, Example 3, and Comparative Example A.

TABLE 1

| Component | Example 1 | Example 2 | Example 3 | Comp. Example A |
|---|---|---|---|---|
| Sodium carbonate, wt. % | 54.6 | 54.55 | 51.55 | 57.21 |
| Sodium bicarbonate, wt. % | 2.88 | 2.88 | 2.88 | 2.88 |
| Anhydrous metasilicate, wt. % | 3 | 3 | 3 | 3 |
| Builder, wt. % | 20 | 20 | 20 | 20 |
| Copolymer, wt. % | 0.98 | 1.98 | 0.98 | 1.98 |
| Nonionic surfactant, wt. % | 3.53 | 3.53 | 3.53 | 3.53 |
| Defoamer, wt. % | 1.06 | 1.06 | 1.06 | 1.06 |
| Sodium citrate dihydrate, wt. % | 5.19 | 0.00 | 0.00 | 0.00 |
| Sodium tartrate dihydrate, wt. % | 0.00 | 1.4 | 0.00 | 0.00 |
| Sodium acetate, wt. % | 0.00 | 0.00 | 9.39 | 0.00 |
| Water, wt. % | 8.76 | 12.6 | 7.61 | 11.34 |

The compositions of Examples 1, 2, and 3 and Comparative Example A were then subjected to the dimensional stability test for formed products, as discussed above, to observe the dimensional stability of the compositions after heating. The results are tabulated below in Table 2.

TABLE 2

| | | Initial | Post-heating | % Growth |
|---|---|---|---|---|
| Example 1 | Diameter, mm | 15.17 | 45.33 | 0.3 |
| | Height, mm | 19.15 | 19.17 | 0.1 |
| Example 2 | Diameter, mm | 44.69 | 44.86 | 0.4 |
| | Height, mm | 21.03 | 21.07 | 0.1 |
| Example 3 | Diameter, mm | 45.38 | 45.46 | 0.1 |
| | Height, mm | 20 | 20.08 | 0.4 |
| Comparative | Diameter, mm | 44.77 | 46 | 2.7 |
| Example A | Height, mm | 19.38 | 20.96 | 8.2 |

As illustrated in Table 2, the formed products of the compositions of Examples 1, 2, and 3 exhibited considerably less swelling than the formed product of the composition of Comparative Example A. In particular, the product of the composition of Example 1 had only a 0.3% growth in diameter and a 0.1% growth in height, the product of the composition of Example 2 only had a 0.4% growth in diameter and a 0.1% growth in height, and the product of the composition of Example 3 only had a 0.1% growth in diameter and a 0.4% growth in height. By comparison, the product of the composition of Comparative Example A had a 2.7% growth in diameter and an 8.2% growth in height.

The only difference in the compositions of Examples 1, 2, and 3 and Comparative Example A was the presence of a straight chain saturated mono-, di-, or tri-carboxylic acid salt. It is thus believed that the straight chain saturated mono-, di-, or tri-carboxylic acid salt aided in the dimensional stability of the products of the compositions of Example 1, Example 2, and Example 3. By controlling the migration of water and acting as a donor or acceptor of free water, the straight chain saturated mono-, di-, or tri-carboxylic acid salt may have allowed processing and prevented the formed products from swelling when the products were subjected to heat as well as controlled the rate of solidification of the product within the desired range. Because the composition of Comparative Example A did not contain a straight chain saturated mono-, di-, or tri-carboxylic acid salt, the composition did not include a mechanism for controlling the movement of water within the solid product. The composition of Comparative Example A would not be suitable for processing and failed the test for dimensional stability.

The following test method was used to characterize the compositions produced in Examples 4, 5, and 6 and Comparative Example B:

Dimensional Stability Test for Cast Products

Approximately 4000 grams batch of the product using a straight chain saturated mono-, di-, or tri-carboxylic acid salt as part of the solidification matrix was first poured into a capsule. The diameter of the capsule was measured and recorded. The capsule was maintained at room temperature for one day, held in an oven at a temperature of approximately 104° F. for two days, and then returned to room temperature. After the capsule returned to room temperature, the diameter of the capsule was measured and recorded. The capsule was considered to exhibit dimensional stability if there was less than approximately 2% swelling, or growth.

Examples 4, 5, and 6 and Comparative Example B

Examples 4, 5, and 6 are compositions of the present invention using a straight chain saturated mono-, di-, or tri-carboxylic acid salt as a part of the solidification matrix. In particular, the composition of Example 4 used sodium citrate dihydrate as part of the solidification matrix, the composition of Example 5 used sodium tartrate dihydrate as part of the solidification matrix, and the composition of Example 6 used sodium acetate as part of the solidification matrix. Each of the compositions of Examples 4-6 also included component concentrations (in weight percent) of softened water, aminocarboxylate, sodium polyacrylate, sodium hydroxide 50%, sodium carbonate (dense ash), anionic surfactant, and nonionic surfactant, as provided in Table 3. The liquids (softened water, aminocarboxylate, straight chain saturated mono-, di-, or tri-carboxylic acid salt, polyacrylate, and sodium hydroxide 50%) were premixed in order to form a liquid premix and the powders (sodium carbonate, anionic surfactant, and nonionic surfactant) were premixed in order to form a powder premix. The liquid premix and the powder premix were then mixed to form the composition, which was subsequently poured into capsules.

The composition of Comparative Example B was prepared as in Examples 4, 5, and 6 except that the composition of Comparative Example B did not contain a straight chain saturated mono-, di-, or tri-carboxylic acid salt but did contain the same quantity of available water.

Table 3 provides the component concentrations for the compositions of Examples 4-6 and Comparative Example B.

TABLE 3

| Component | Example 4 | Example 5 | Example 6 | Comp. Example B |
|---|---|---|---|---|
| Water, softened, wt. % | 32.00 | 28.03 | 28.03 | 28.03 |
| Sodium citrate dihydrate, wt. % | 0.00 | 4.00 | 0.00 | 0.00 |
| Sodium tartrate dihydrate | 4.00 | 0.00 | 0.00 | 0.00 |
| Sodium acetate, wt. % | 0.00 | 0.00 | 4.00 | 0.00 |
| Aminocarboxylate wt. % | 0.00 | 3.00 | 3.00 | 3.00 |
| Sodium polyacrylate, wt. % | 0.75 | 0.75 | 0.75 | 0.75 |
| NaOH, 50%, wt. % | 0.33 | 0.33 | 0.33 | 0.33 |
| Sodium carbonate, wt. % | 57.92 | 58.89 | 58.89 | 62.89 |
| Anionic surfactant, wt. % | 1.00 | 1.00 | 1.00 | 1.00 |
| Nonionic surfactant, wt. % | 4.00 | 4.00 | 4.00 | 4.00 |

After the compositions of Example 4-6 and Comparative Example B were formed, they were subjected to the dimensional stability test for cast products, as discussed above, to observe the dimensional stability of the compositions after heating. The results are tabulated below in Table 4.

TABLE 4

| | | Initial | Post-heating | % Growth |
|---|---|---|---|---|
| Example 4 | Diameter, mm | 161 | 163 | 1.2 |
| Example 5 | Diameter, mm | 160 | 161 | 0.6 |
| Example 6 | Diameter, mm | 160 | 162 | 1.2 |
| Comparative Example B | Diameter, mm | 162 | 170 | 4.9 |

As illustrated in Table 4, the cast products of the compositions of Example 4-6 exhibited considerably less swelling than the cast product of the composition of Comparative Example B. In particular, the product of the composition of Example 4 experienced only a 1.2% growth in diameter, the product of the composition of Example 5 experienced only a 0.6% growth in diameter, and the product of the composition of Example 6 experienced only a 1.2% growth in diameter. By comparison, the product of the composition of Comparative Example B had a 4.9% growth in diameter.

The only difference in the compositions of Examples 4-6 and Comparative Example B was the presence of a straight chain saturated mono-, di-, or tri-carboxylic acid salt. It is thus believed that the straight chain saturated mono-, di-, or tri-carboxylic acid salt aided in the dimensional stability of the products of the compositions of Examples 4-6. By controlling the migration of water and acting as a donor or acceptor of free water, the straight chain saturated mono-, di-, or tri-carboxylic acid salt may have allowed processing and prevented the cast product from swelling when the product was subjected to heat as well as controlled the rate of solidification of the product within the desired range. By contrast, because the composition of Comparative Example B did not contain a straight chain saturated mono-, di-, or tri-carboxylic acid salt, the composition did not contain a mechanism for controlling the movement of water within the solid product. The composition of Comparative Example B failed the test for dimensional stability and would not be suitable for manufacture.

Although the present invention has been described with reference to preferred embodiments, workers skilled in the art will recognize that changes may be made in form and detail without departing from the spirit and scope of the invention.

The invention claimed is:

1. A solidification matrix consisting essentially of:

(a) a straight chain saturated carboxylic acid salt selected from the group consisting of: acetic acid, gluconic acid, malic acid, succinic acid, glutaric acid, adipic acid, tartartic acid, and citric acid;

(b) sodium carbonate; and (c) water;

(d) wherein the solidification matrix is a hydrate solid;

(e) wherein if heated at a temperature of 120 degrees Fahrenheit, the solidification matrix is dimensionally stable and has a growth exponent of less than 2%; and (f) wherein the solidification matrix is phosphorous-free and NTA-free.

2. The solidification matrix of claim 1, wherein the straight chain saturated carboxylic acid salt constitutes between about 1% and about 15% by weight of the solidification matrix.

3. The solidification matrix of claim 1, wherein the sodium carbonate constitutes between about 20% and about 70% by weight of the solidification matrix.

4. The solidification matrix of claim 1, wherein the water constitutes between about 2% and about 50% by weight of the solidification matrix.

5. A solid detergent composition comprising:

(a) between about 1% and about 15% straight chain saturated mono-, di-, or tri-carboxylic acid salt by weight of the solid detergent composition, wherein the salt of the straight chain saturated mono, di-, or tri-carboxylic acid salt is selected from the group consisting of: acetic acid, gluconic acid, malic acid, succinic acid, glutaric acid, adipic acid, tartartic acid, and citric acid;

(b) between about 2% and about 50% water by weight of the solid detergent composition;

(c) less than about 40% builder by weight of the solid detergent composition;

(d) between about 20% and about 70% sodium carbonate by weight of the solid detergent composition;

(e) between about 0.5% and about 10% surfactant by weight of the solid detergent composition;

(f) less than about 0.5% phosphorous containing compounds by weight of the solid detergent composition; and (g) less than about 0.5% NTA containing compounds by weight of the solid detergent composition;

(h) wherein if heated at a temperature of 120 degrees Fahrenheit, the solid detergent composition is dimensionally stable and has a growth exponent of less than 2%.

6. The solid detergent composition of claim 5, wherein the straight chain saturated mono-, di-, or tri-carboxylic acid salt constitutes between about 1% and about 10% by weight of the solid detergent composition.

7. The solid detergent composition of claim 5, wherein the water constitutes between about 5% and about 40% by weight of the solid detergent composition.

8. The solid detergent composition of claim 5, wherein the builder constitutes less than about 30% by weight of the solid detergent composition.

9. The solid detergent composition of claim 5, wherein the sodium carbonate constitutes between about 45% and about 65% by weight of the solid detergent composition.

10. The solid detergent composition of claim 5, wherein the surfactant constitutes between about 1% and about 5% by weight of the solid detergent composition.

11. A solid block detergent composition comprising:

(a) between about 1% and about 15% sodium citrate by weight of the solid detergent block composition;

(b) between about 2% and about 50% water by weight of the solid block detergent composition;

(c) less than about 40% builder by weight of the solid detergent block composition;

(d) between about 20% and about 70% sodium carbonate by weight of the solid block detergent composition;

(e) between about 0.5% and about 10% surfactant by weight of the solid block detergent composition;

(f) less than about 0.5% phosphorous containing compounds by weight of the solid detergent composition; and (g) less than about 0.5% NTA containing compounds by weight of the solid detergent composition;

(h) wherein if heated at a temperature of 120 degrees Fahrenheit, the solid block detergent composition is dimensionally stable and has a growth exponent of less than 2%.

12. A composition consisting essentially of:

(a) a solidification matrix comprising a salt of a straight chain saturated mono-, di-, or tri-carboxylic acid, sodium carbonate, and water, wherein the straight chain saturated mono-, di-, or tri-carboxylic acid is selected from the group consisting of acetic acid, gluconic acid, malic acid, succinic acid, glutaric acid, adipic acid, tartic acid, and citric acid; and (b) at least one functional ingredient;

(c) wherein if heated at a temperature of 120 degrees Fahrenheit, the composition has a growth exponent of less than 2% and is dimensionally stable; and (d) wherein the composition is substantially free of phosphorous containing compounds and NTA containing compounds.

13. The composition of claim 12, wherein the functional ingredient is selected from the group consisting of: chelating agents, sequestering agents, inorganic detergents, organic detergents, alkaline sources, surfactants, rinse aids, bleaching agents, sanitizers, activators, detergent builders, fillers, defoaming agents, anti-redeposition agents, optical brighteners, dyes, odorants, enzymes, corrosion inhibitors, dispersants, and solubility modifiers.

14. The composition of claim 12, wherein the salt of the straight chain saturated mono-, di-, or tri-carboxylic acid constitutes between about 1% and about 15% by weight of the solidification matrix.

15. A method of solidifying a composition, the method comprising:

(a) adding a solidification matrix to the composition, the solidification matrix consisting essentially of a straight chain saturated mono-, di-, or tri-carboxylic acid salt, sodium carbonate, and water to form a hydrate solid, wherein the straight chain saturated mono-, di-, or tri-carboxylic acid is selected from the group consisting of acetic acid, gluconic acid, malic acid, succinic acid, glutaric acid, adipic acid, tartartic acid, and citric acid, wherein the composition includes less than about 0.5% phosphorous containing compounds by weight of the composition and less than about 0.5% NTA containing compounds by weight of the composition; and (b) solidifying the composition for between about 1 minute and about 3 hours to form a solid composition that, if subjected to a temperature of 120 degrees Fahrenheit, is dimensionally stable and has a growth exponent of less than 2%.

16. The method of claim 15, wherein the composition solidifies in between about 1 minute and about 2 hours.

17. The method of claim 16, wherein the composition solidifies in between about 1 minute and about 20 minutes.

18. The method of claim 15, wherein the straight chain saturated mono-, di-, or tri-carboxylic acid salt constitutes between about 1% and about 15% by weight of the solidification matrix.

19. The method of claim 15, wherein the straight chain saturated mono-, di-, or tri-carboxylic acid salt and water of the solidification matrix are provided as a liquid premix.

* * * * *